United States Patent
Jiang et al.

(10) Patent No.: US 9,228,929 B2
(45) Date of Patent: Jan. 5, 2016

(54) METHOD OF ON-LINE RAPID FLUID DENSITY MEASUREMENT USING A PIEZORESISTIVE MICRO-CANTILEVER

(71) Applicant: XI'AN JIAOTONG UNIVERSITY, Shaanxi (CN)

(72) Inventors: Zhuangde Jiang, Shaanxi (CN); Guiming Zhang, Shaanxi (CN); Libo Zhao, Shaanxi (CN); Enze Huang, Shaanxi (CN); Longqi Xu, Shaanxi (CN); Yulong Zhao, Shaanxi (CN); Xiaopo Wang, Shaanxi (CN); Bo Song, Shaanxi (CN); Zhigang Liu, Shaanxi (CN)

(73) Assignee: XI'AN JIAOTONG UNIVERSITY, Shaanxi (CN)

( * ) Notice: Subject to any disclaimer, the term of this patent is extended or adjusted under 35 U.S.C. 154(b) by 744 days.

(21) Appl. No.: 13/658,639

(22) Filed: Oct. 23, 2012

(65) Prior Publication Data
US 2013/0261995 A1    Oct. 3, 2013

Related U.S. Application Data

(63) Continuation of application No. PCT/CN2012/073424, filed on Mar. 31, 2012.

(51) Int. Cl.
*G01N 9/00* (2006.01)
*G01N 27/74* (2006.01)
*G01N 29/036* (2006.01)
(Continued)

(52) U.S. Cl.
CPC *G01N 9/002* (2013.01); *G01N 9/32* (2013.01); *G01N 27/74* (2013.01); *G01N 29/036* (2013.01); *G01N 29/222* (2013.01);
(Continued)

(58) Field of Classification Search
CPC ............ G01N 9/002; G01N 2009/006; G01N 29/036; G01N 2291/02818; G01N 2291/014; G01N 29/222; G01N 9/32; G01N 2291/022; G01N 27/74
USPC .......................................................... 702/53
See application file for complete search history.

(56) References Cited

U.S. PATENT DOCUMENTS 5,663,507 A * 9/1997 Westervelt ................ G01L 1/16
                                                         73/727
6,311,549 B1 * 11/2001 Thundat ................. G01N 9/002
                                                         73/24.05
(Continued)

FOREIGN PATENT DOCUMENTS

CN    101718667 A  *  6/2010
CN    101738355 A  *  6/2010
(Continued)

*Primary Examiner* — John Breene
*Assistant Examiner* — Eyob Hagos
(74) *Attorney, Agent, or Firm* — J.C. Patents

(57) ABSTRACT

The present invention provides a method of on-line rapid fluid density measurement using a piezoresistive micro-cantilever, the present invention can achieve on-line measurement without changing the existing device; more importantly, without acquiring the resonant frequency of the cantilever in fluid to be detected, thus remarkably reducing measurement time, and guaranteeing the real on-line rapid measurement. By using the method of the present invention, measurement of the density of fluid to be detected by a calibrated piezoresistive micro-cantilever may be achieved within seconds or even shorter.

5 Claims, 3 Drawing Sheets

(51) Int. Cl.
*G01N 29/22* (2006.01)
*G01N 9/32* (2006.01)

(52) U.S. Cl.
CPC ... *G01N 2009/006* (2013.01); *G01N 2291/014* (2013.01); *G01N 2291/02818* (2013.01)

(56) References Cited

U.S. PATENT DOCUMENTS

| | | | | |
|---|---|---|---|---|
| 7,434,457 B2 * | 10/2008 | Goodwin | ............... | E21B 49/08 361/160 |
| 7,762,124 B2 * | 7/2010 | Okaguchi | ............ | G01N 29/022 73/61.49 |
| 8,689,614 B2 * | 4/2014 | Day | ...................... | G01N 9/002 435/13 |
| 8,751,172 B2 * | 6/2014 | Puchades | ............... | G01N 9/002 702/50 |
| 8,845,968 B2 * | 9/2014 | Day | ...................... | G01N 9/002 422/430 |
| 2005/0276726 A1 * | 12/2005 | McGill | ................ | G01N 29/036 422/96 |
| 2008/0034840 A1 * | 2/2008 | Mutharasan | ......... | G01N 29/022 73/24.01 |
| 2008/0065225 A1 * | 3/2008 | Wasielewski | ............ | A61B 5/03 623/18.11 |
| 2009/0084178 A1 * | 4/2009 | Sinha | ................... | G01N 11/167 73/32 A |
| 2011/0077872 A1 * | 3/2011 | Loui | ...................... | G01N 25/18 702/24 |
| 2012/0094270 A1 * | 4/2012 | Mutharasan | ........... | G01H 11/08 435/5 |

FOREIGN PATENT DOCUMENTS

| | | | |
|---|---|---|---|
| CN | 101809420 | A | 8/2010 |
| CN | 101738355 | B | 8/2011 |
| CN | 101718667 | B | 11/2011 |
| CN | 102288516 | A | 12/2011 |
| CN | 102288516 | A * | 12/2011 |
| CN | 102353609 | A | 2/2012 |
| CN | 102353609 | A * | 2/2012 |

* cited by examiner

METHOD OF ON-LINE RAPID FLUID DENSITY MEASUREMENT USING A PIEZORESISTIVE MICRO-CANTILEVER

CROSS-REFERENCE TO RELATED APPLICATIONS

This application is a continuation of International Application No. PCT/CN2012/073424, filed on Mar. 31, 2012. The contents of the above identified applications are incorporated herein by reference in their entirety.

FIELD OF THE TECHNOLOGY

The present invention relates to a method of fluid density measurement, and particularly, to a method of on-line rapid fluid density measurement using a piezoresistive micro-cantilever.

BACKGROUND

A micro-cantilever, with the advantages of high sensitivity, fast response, small size, mass production and real-time measurement etc, has been widely used in measurement fields such as chemistry, physics and biology. The micro-cantilever has two operation modes, static and dynamic. The former is achieved by mainly measuring the deflection at an end of the cantilever, and used for such as measuring surface stress, concentration of a substance, etc. The latter is achieved by mainly measuring the resonant frequency of the cantilever in working environment, and used for such as measuring molecular weight of an organism, fluid viscosity and density, etc. The peizoresistive micro-cantilever, without the need of alignment, which is necessary for an optical cantilever, can integrate a detection system upon the cantilever so as to significantly reduce the size of the measurement device. Thus, the peizoresistive micro-cantilever is widely used in Micro-Electro-Mechanical Systems. To measure the density of a fluid with a peizoresistive micro-cantilever, there is a need to acquire the resonant frequency of the cantilever in fluid to be detected. This greatly increases measurement time (more than one minute), and is not suitable for the on-site fluid density measurement, in particular for those fluids that need real time monitoring.

In view of the above disadvantages, there is a need to provide a method of on-line rapid fluid density measurement using a piezoresistive micro-cantilever, so as to reduce measurement time.

SUMMARY

The present invention aims at providing a method of on-line rapid fluid density measurement using a piezoresistive micro-cantilever, without changing the existing measurement device, and without acquiring the resonant frequency of the cantilever in fluid to be detected, so as to achieve the aim of on-line rapid fluid density measurement.

In order to overcome the disadvantages of the existing method, the present invention provides a method of on-line rapid fluid density measurement using a piezoresistive micro-cantilever, comprising the following steps:

(1) submerge a piezoresistive micro-cantilever into a standard fluid of known density $p_1$, then provide a sinusoidal alternating voltage of frequency f and amplitude $U_1$ to an excitation coil (9) of the piezoresistive micro-cantilever via a first and a second bonding pads (1,2), supply, by a Wheatstone bridge (8), a constant-current source via a third, a fifth, and a sixth bonding pads (3,5,6), measure an output of the Wheatstone bridge (8) via a fourth and a seventh bonding pads (4,7) using a lock-in amplifier and get a result $V_1$;

(2) provide another sinusoidal alternating voltage of frequency f and amplitude $U_2$ to the excitation coil (9) of the piezoresistive micro-cantilever via the first and second bonding pads (1,2), measure the output of the Wheatstone bridge (8) using the lock-in amplifier and get a result $V_2$;

(3) change the density of the standard fluid into $p_2$ by increasing or decreasing temperature, then provide a sinusoidal alternating voltage of frequency f and amplitude $U_1$ to the excitation coil (9) of the piezoresistive micro-cantilever via the first and second bonding pads (1,2), measure the output of the Wheatstone bridge (8) using the lock-in amplifier and get a result $V_3$;

(4) provide another sinusoidal alternating voltage of frequency f and amplitude $U_2$ to the excitation coil (9) of the piezoresistive micro-cantilever via the first and second bonding pads (1,2), measure the output of the Wheatstone bridge (8) using the lock-in amplifier and get a result $V_4$;

(5) in accordance with the above measuring results and a density equation p=ak+b, calculate parameters a and b of the density equation, wherein, k is a ratio of output voltage difference of the Wheatstone bridge to voltage difference of the excitation coil (9) before and after the voltage change of the excitation coil (9), that is, $k_1=(V_1-V_2)/(U_1-U_2)$, $k_2=(V_3-V_4)/(U_1-U_2)$, solve a system of equations $p_1=ak_1+b$ and $p2=ak_2+b$, and then obtain the parameters a and b; and it should be pointed that a and b only relate to the structure of the micro-cantilever itself, the frequency of an input voltage of the excitation coil, the magnitude of the supply current of the Wheatstone bridge and the intensity of an external magnetic field, and won't change with the change of fluid to be detected and the amplitude of the input voltage;

(6) submerge the piezoresistive micro-cantilever into a fluid to be detected, then provide a sinusoidal alternating voltage of frequency f and amplitude $U_1$ to the excitation coil (9) of the piezoresistive micro-cantilever via the first and second bonding pads (1,2), measure the output of the Wheatstone bridge (8) using the lock-in amplifier and get a result $V_5$; provide another sinusoidal alternating voltage of frequency f and amplitude $U_2$ to the excitation coil (9) of the piezoresistive micro-cantilever via the first and second bonding pads, measure the output of the Wheatstone bridge (8) using the lock-in amplifier and get a result $V_6$; in accordance with the above measuring results, determine the value of $k_3$, $k_3=(V_5-V_6)/(U_1-U_2)$, and then determine the density of the fluid to be detected based on the density equation p=ak+b.

The piezoresistive micro-cantilever of the present invention utilizes electromagnetic excitation, an external magnetic field is provided by a permanent magnet. For a calibrated piezoresistive micro-cantilever, the magnitude of the supply current of the Wheatstone bridge, the frequency of the input voltage of the excitation coil or the intensity of the magnetic field of the permanent magnet should not be changed.

The permanent magnet can be a samarium-cobalt permanent magnet.

The piezoresistive micro-cantilever may be of a common rectangular shape, may also be of a triangular shape, a trapezoidal shape or of any other shape.

The method of on-line rapid fluid density measurement using a piezoresistive micro-cantilever of the present invention at least has the following advantages: an on-line measurement without changing the existing device can be achieved; more importantly, there is no need to acquire the resonant frequency of the cantilever in the fluid to be detected, thus remarkably reducing measurement time, and guaranteeing the real on-line rapid measurement. By using the method of the present invention, measurement of the density of fluid to be detected by a calibrated piezoresistive micro-cantilever may be achieved within seconds or even shorter.

Figure 1:
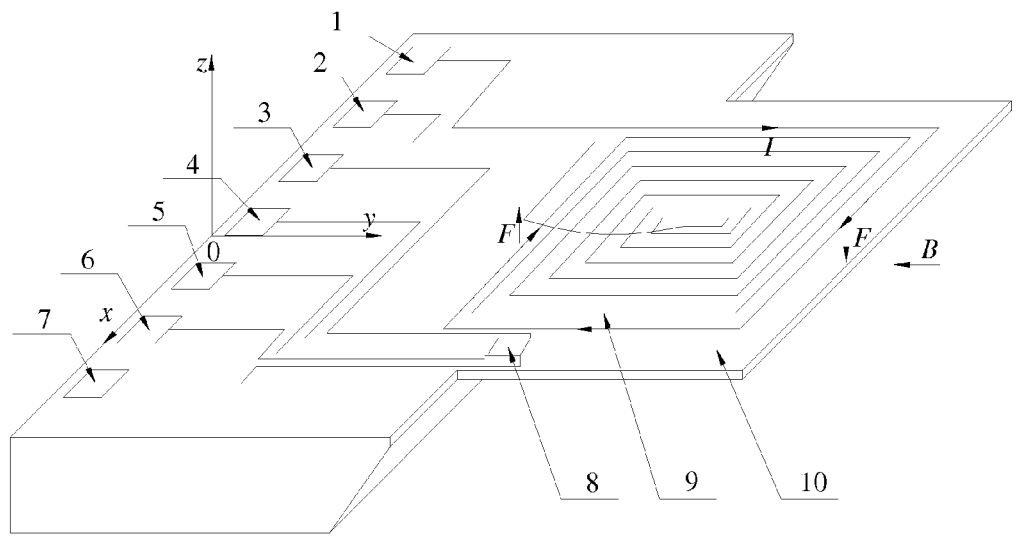
FIG. 1 is a schematic diagram of a plane structure of a piezoresistive micro-cantilever of the present invention.

Reference numerals of diagrams are as follows:

| 1-7 | First to seventh bonding pads | 8 | Wheatstone bridge |
|---|---|---|---|
| 9 | Excitation coil | 10 | Rectangular cantilever |
| 11 | Triangular cantilever | 12 | Trapezoidal cantilever |
| 13 | Arbitrary cantilever | | |

DETAILED DESCRIPTION

The following detailed description is given in conjunction with the accompanying drawings to the working principle of the method of on-line rapid fluid density measurement using a piezoresistive micro-cantilever of the present invention:

As shown in FIG. 1, a method of on-line rapid fluid density measurement using a piezoresistive micro-cantilever of the present invention comprises the following steps:

(1) submerge a piezoresistive micro-cantilever into a standard fluid of known density $p_1$, then provide a sinusoidal alternating voltage of frequency f and amplitude $U_1$ to an excitation coil 9 of the piezoresistive micro-cantilever via a first and a second bonding pads 1,2, supply, by a Wheatstone bridge 8, a constant-current source via a third, a fifth, and a sixth bonding pads 3,5,6, measure an output of the Wheatstone bridge 8 via a fourth and a seventh bonding pads 4,7 using a lock-in amplifier and get a result $V_1$;

(2) provide another sinusoidal alternating voltage of frequency f and amplitude $U_2$ to the excitation coil 9 of the piezoresistive micro-cantilever via the first and second bonding pads 1,2, measure the output of the Wheatstone bridge 8 using the lock-in amplifier and get a result $V_2$;

(3) change the density of the standard fluid into $p_2$ by increasing or decreasing temperature, then provide a sinusoidal alternating voltage of frequency f and amplitude $U_1$ to the excitation coil 9 of the piezoresistive micro-cantilever via the first and second bonding pads 1,2, measure the output of the Wheatstone bridge 8 using the lock-in amplifier and get a result $V_3$;

(4) provide another sinusoidal alternating voltage of frequency f and amplitude $U_2$ to the excitation coil 9 of the piezoresistive micro-cantilever via the first and second bonding pads 1,2, measure the output of the Wheatstone bridge 8 using the lock-in amplifier and get a result $V_4$;

(5) in accordance with the above measuring results and a density equation p=ak+b, calculate parameters a and b of the density equation, wherein, k is a ratio of output voltage difference of the Wheatstone bridge to voltage difference of the excitation coil 9 before and after the voltage change of the excitation coil 9, that is, $k_1=(V_1-V_2)/(U_1-U_2)$, $k_2=(V_3-V_4)/(U_1-U_2)$, solve a system of equations $p_1=ak_1+b$ and $P_2=ak_2+b$, and then obtain the parameters a and b;

(6) submerge the piezoresistive micro-cantilever into a fluid to be detected, then provide a sinusoidal alternating voltage of frequency f and amplitude $U_1$ to the excitation coil 9 of the piezoresistive micro-cantilever via the first and second bonding pads 1,2, measure the output of the Wheatstone bridge 8 using the lock-in amplifier and get a result $V_5$; provide another sinusoidal alternating voltage of frequency f and amplitude $U_2$ to the excitation coil 9 of the piezoresistive micro-cantilever via the first and second bonding pads, measure the output of the Wheatstone bridge 8 using the lock-in amplifier and get a result $V_6$; in accordance with the above measuring results, determine the value of $k_3$, $k_3=(V_5-V_6)/(U_1-U_2)$, and then determine the density of the fluid to be detected based on the density equation p=ak+b.

Here, it should be specially pointed out that, the piezoresistive micro-cantilever of the present invention utilizes electromagnetic excitation, an external magnetic field is provided by a permanent magnet, preferably a samarium-cobalt permanent magnet. For the calibrated piezoresistive micro-cantilever, the magnitude of the supply current of Wheatstone bridge, the frequency of the input voltage of excitation coil or the intensity of the magnetic field of a permanent magnet should not be changed.

Figure 2:
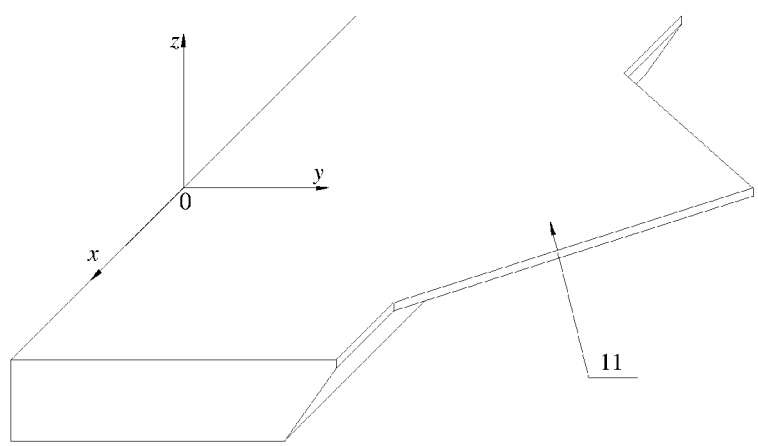
FIG. 2 is a schematic structural diagram of a triangular piezoresistive micro-cantilever of the present invention.
Figure 3:
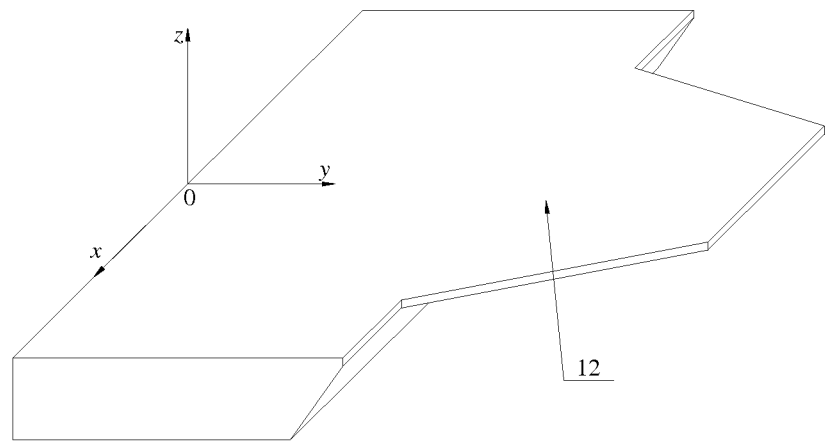
FIG. 3 is a schematic structural diagram of a trapezoidal piezoresistive micro-cantilever of the present invention.
Figure 4:
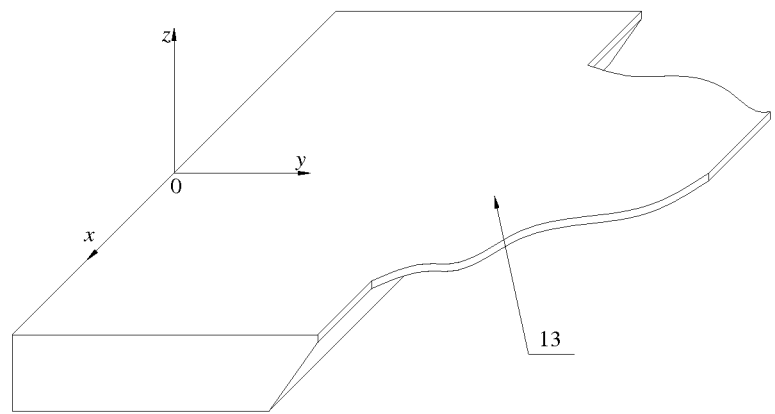
FIG. 4 is a schematic structural diagram of an arbitrary piezoresistive micro-cantilever of the present invention.

As shown in FIGS. 2, 3, 4, the piezoresistive micro-cantilever may be of a common rectangular shape 10, may also be of a triangular shape 11, a trapezoidal shape 12 or of any other shape 13.

Figure 5:
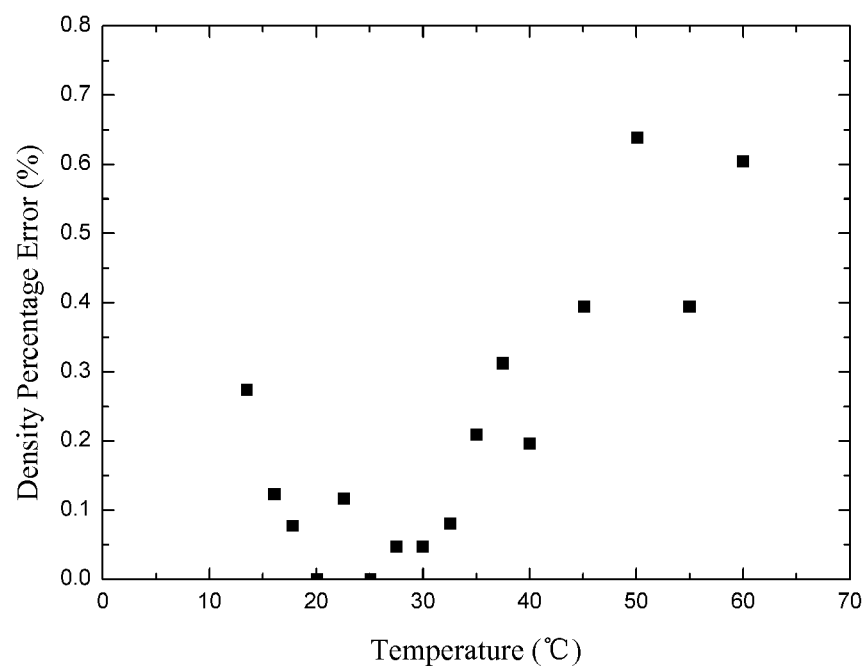
FIG. 5 is an experimental data diagram of the present invention.

FIG. 5 is an experimental data diagram of the present invention, the cantilever used is a trapezoidal piezoresistive micro-cantilever, the fluid to be detected is silicone oil, the measurement temperature range is 10-60, the measurement pressure is an atmospheric pressure, the frequency of supply voltage of excitation coil of the micro-cantilever is 60 kHz, the supply current of Wheatstone bridge is 2 mA, the measurement accuracy of the density is within 1% FS, and a single measurement time is 3 seconds.

The content above is merely an embodiment of the present invention, not all the embodiments or an exclusive embodiment of the present invention, any equivalent alternations and modifications by those skilled in the art upon reading specification of the present invention, shall fall within the scope as defined by claims of the present invention.

What is claimed is:

1. A method of on-line rapid fluid density measurement using a piezoresistive micro-cantilever, comprising the following steps:

(1) submerge a piezoresistive micro-cantilever into a standard fluid of known density $p_1$, then provide a sinusoidal alternating voltage of frequency f and amplitude $U_1$ to an excitation coil (9) of the piezoresistive micro-cantilever via a first and a second bonding pads (1,2), supply, by a Wheatstone bridge (8), a constant-current source via a third, a fifth, and a sixth bonding pads (3,5,6), measure an output of the Wheatstone bridge (8) via a fourth and a seventh bonding pads (4,7) using a lock-in amplifier and get a result $V_1$;

(2) provide another sinusoidal alternating voltage of frequency f and amplitude $U_2$ to the excitation coil (9) of the piezoresistive micro-cantilever via the first and second bonding pads (1,2), measure the output of the Wheatstone bridge (8) using the lock-in amplifier and get a result $V_2$;

(3) change the density of the standard fluid into $p_2$ by increasing or decreasing temperature, then provide a sinusoidal alternating voltage of frequency f and amplitude $U_1$ to the excitation coil (9) of the piezoresistive micro-cantilever via the first and second bonding pads (1,2), measure the output of the Wheatstone bridge (8) using the lock-in amplifier and get a result $V_3$;

(4) provide another sinusoidal alternating voltage of frequency f and amplitude $U_2$ to the excitation coil (9) of the piezoresistive micro-cantilever via the first and second bonding pads (1,2), measure the output of the Wheatstone bridge (8) using the lock-in amplifier and get a result $V_4$;

(5) in accordance with the above measuring results and a density equation p=ak+b, calculate parameters a and b of the density equation, wherein, k is a ratio of output voltage difference of the Wheatstone bridge to voltage difference of the excitation coil (9) before and after the voltage change of the excitation coil (9), that is, $k_1=(V_1-V_2)/(U_1-U_2)$, $k_2=(V_3-V_4)/(U_1-U_2)$, solve a system of equations $p_1=ak_1+b$ and $P2=ak_2+b$, and then obtain the parameters a and b;

(6) submerge the piezoresistive micro-cantilever into a fluid to be detected, then provide a sinusoidal alternating voltage of frequency f and amplitude $U_1$ to the excitation coil (9) of the piezoresistive micro-cantilever via the first and second bonding pads (1,2), measure the output of the Wheatstone bridge (8) using the lock-in amplifier and get a result $V_5$; provide another sinusoidal alternating voltage of frequency f and amplitude $U_2$ to the excitation coil (9) of the piezoresistive micro-cantilever via the first and second bonding pads, measure the output of the Wheatstone bridge (8) using the lock-in amplifier and get a result $V_6$; in accordance with the above measuring results, determine the value of $k_3$, $k_3=(V_5-V_6)/(U_1-U_2)$, and then determine the density of the fluid to be detected based on the density equation p=ak+b.

2. A method of on-line rapid fluid density measurement using a piezoresistive micro-cantilever, comprising:

(1) submerge the piezoresistive micro-cantilever into a standard fluid of known density $p_1$, supply a Wheatstone bridge with a constant current source, and then apply a sinusoidal alternating voltage to an excitation coil (9) of the piezoresistive micro-cantilever, wherein the sinusoidal alternating voltage has frequency f and amplitude $U_1$, and get output $V_1$ of the Wheatstone bridge; (2) change the amplitude of the alternating voltage applied to the excitation coil (9) of the piezoresistive micro-cantilever to $U_2$, and get output $V_2$ of the Wheatstone bridge; (3) change the density of the standard fluid into $p_2$, repeat steps (1) and (2), and get output $V_3$ and $V_4$ of the Wheatstone bridge, respectively; (4) solve a system of equations $p_1=ak_1+b$ and $p2=ak_2+b$, and determine parameters a and b, wherein $k_1=(V_1-V_2)/(U_1-U_2)$, $k_2=(V_3-V_4)/(U_1-U_2)$; (5) submerge the piezoresistive micro-cantilever into a fluid to be detected, repeat steps (1) and (2), and get output $V_5$ and $V_6$ of the Wheatstone bridge, respectively, and then determine the density of the fluid to be detected based on the equation p=ak+b, wherein $k=(V_5-V_6)/(U_1-U_2)$.

3. The method of on-line rapid fluid density measurement using a piezoresistive micro-cantilever as claimed in claim 2, wherein:

the piezoresistive micro-cantilever is of a rectangular shape or a triangular shape or a trapezoidal shape or of any other shape.

4. The method of on-line rapid fluid density measurement using a piezoresistive micro-cantilever as claimed in claim 1, wherein:

the piezoresistive micro-cantilever utilizes electromagnetic excitation, and an external magnetic field is provided by a permanent magnet.

5. The method of on-line rapid fluid density measurement using a piezoresistive micro-cantilever as claimed in claim 4, wherein:

the permanent magnet can be a samarium-cobalt permanent magnet.

* * * * *